(12) United States Patent
Lytle

(10) Patent No.: US 6,872,221 B2
(45) Date of Patent: Mar. 29, 2005

(54) THERAPEUTIC LOW LEVEL LASER APPARATUS AND METHOD

(76) Inventor: Larry Robert Lytle, 4020 Sunset Dr., Rapid City, SD (US) 57702

(*) Notice: Subject to any disclaimer, the term of this patent is extended or adjusted under 35 U.S.C. 154(b) by 0 days.

(21) Appl. No.: 10/634,210

(22) Filed: Aug. 5, 2003

(65) Prior Publication Data

US 2004/0030370 A1 Feb. 12, 2004

Related U.S. Application Data

(60) Provisional application No. 60/401,103, filed on Aug. 5, 2002.

(51) Int. Cl.[7] .............................................. A61N 5/067
(52) U.S. Cl. ........................... 607/89; 128/898; 607/88; 606/9
(58) Field of Search ..................... 607/88–95; 128/898

(56) References Cited

U.S. PATENT DOCUMENTS

| | | |
|---|---|---|
| 4,649,935 A | 3/1987 | Charmillot et al. |
| 4,765,322 A | 8/1988 | Charmillot et al. |
| 4,930,504 A | 6/1990 | Diamantopoulos et al. |
| 4,951,663 A | 8/1990 | L'Esperance, Jr. |
| 5,358,503 A | 10/1994 | Bertwell et al. |
| 5,464,436 A | 11/1995 | Smith |
| 5,549,660 A | 8/1996 | Mendes et al. |
| 5,616,140 A | 4/1997 | Prescott |
| 5,755,752 A | 5/1998 | Segal |
| 5,800,479 A | 9/1998 | Thiberg |
| 5,830,211 A | 11/1998 | Santana et al. |
| 6,019,482 A | 2/2000 | Everett |
| 6,187,029 B1 * | 2/2001 | Shapiro et al. ............... 607/88 |
| 6,443,978 B1 * | 9/2002 | Zharov ........................ 607/91 |
| 6,602,275 B1 * | 8/2003 | Sullivan ...................... 607/88 |
| 6,702,837 B2 * | 3/2004 | Gutwein ...................... 607/88 |

FOREIGN PATENT DOCUMENTS

WO    WO 01/32262 A1 *  5/2001  .......... A61N/5/067

* cited by examiner

Primary Examiner—Roy D Gibson
Assistant Examiner—Henry M Johnson, III
(74) Attorney, Agent, or Firm—Ancel W. Lewis, Jr.

(57) ABSTRACT

Apparatus for therapeutic low level laser treatment has a diode array with sets of laser diodes of three wavelengths, and with light emitting diodes of four wavelengths. The emitted laser and light beams overlap in a selected configuration. The method includes pulsing the diodes in one of several available selected frequency sequences. One of the available frequency sequences includes increasing frequency pulsing.

17 Claims, 1 Drawing Sheet

THERAPEUTIC LOW LEVEL LASER APPARATUS AND METHOD

This application claims the benefit under 35 U.S.C. § 119(e) of the U.S. provisional patent application No. 60/401,103 filed Aug. 5, 2002.

TECHNICAL FIELD

The present invention relates to therapeutic lasers, and more particularly to a method and apparatus for programmable, multi-frequency, multi-wavelength low level laser therapy.

BACKGROUND ART

Any living cell in a biological system requires energy for normal metabolism, function, and repair. When injury or sickness occurs, normal metabolism, function, and repair is impaired. The addition of energy delivered directly to damaged areas can aid in the return of normal function.

U.S. Pat. No. 4,930,504 to Diamantopoulos et al. discloses a therapeutic device with a cluster probe connected to a control box. The cluster probe has laser, superluminous and light emitting diodes that emit steady or selectively pulsed radiation in multiple wavelengths to enhance the depth of delivery of energy within the tissue. U.S. Pat. No. 4,951,663 to L'Esperance, Jr. discloses a sterilization device with two laser beams with the phase shift and polarization angle being adjustable between the beams. L'Esperance, Jr. does not suggest any specific beneficial phase shift or polarization angle. The "Resonator" and the "Rotary Multiplex", Low Level Lasers, Inc., are therapeutic devices with a combination of laser and light emitting diodes of multiple wavelengths that are pulsed. The "Rotary Multiplex" includes an increasing pulse frequency program and can be factory reprogrammed.

DISCLOSURE OF THE INVENTION

Therapeutic low level laser apparatus includes a housing, a diode array, control electronics connected to the diode array, and a power source, means for operator input and means for operator output, connected to the control electronics. The diode array has four sets of laser diodes arranged symmetrically about the center of the array, and four pairs of light emitting diodes arranged between the sets of laser diodes. Each set of laser diodes includes first, second and third laser diodes arranged in an equilateral triangle and oriented such that the planes of the linear beams are approximately 120 degrees to each other, intersecting at the center of the triangle. The first, second and third laser diodes emit light of a selected first, second and third wavelength, respectively. The pairs of light emitting diode are arranged in opposed locations about the center of the array and each pair of light emitting diodes emits light of a selected different frequency. The control electronics are programmable and activate the diode array, controlling power output and pulse frequency of each laser and light emitting diode. The therapeutic low level laser method includes providing apparatus that emits a beam of three selected wavelengths of laser light and four selected wavelengths of light emitting diode light, pulsing the beam pursuant to a selected frequency sequence, and exposing tissue to the beam.

BRIEF DESCRIPTION OF THE DRAWINGS

Details of this invention are described in connection with the accompanying drawings that bear similar reference numerals in which.

DETAILED DESCRIPTION OF THE INVENTION

Figure 1:
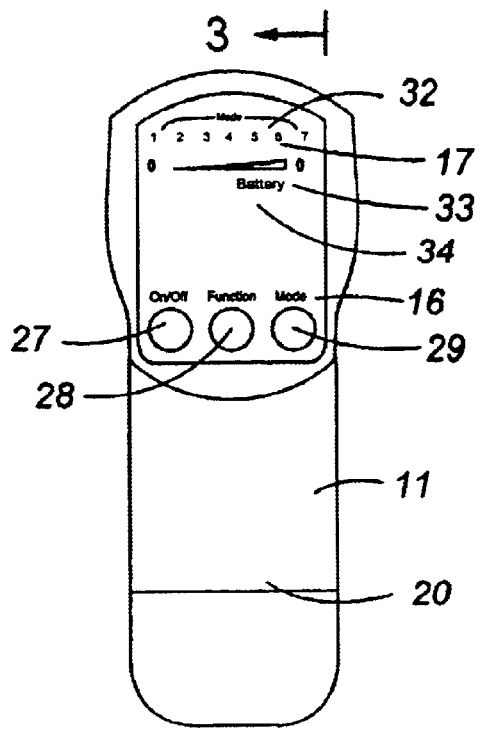
FIG. 1 is a front elevation view of apparatus embodying features of the present invention.
Figure 2:
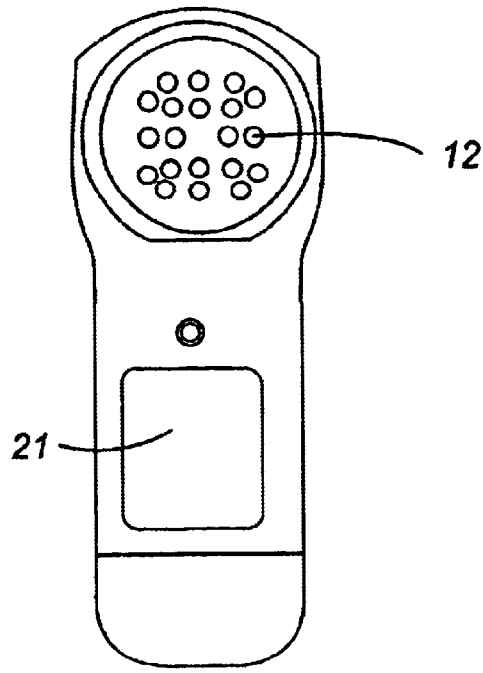
FIG. 2 is a back elevation view of the apparatus of FIG. 1.
Figure 3:
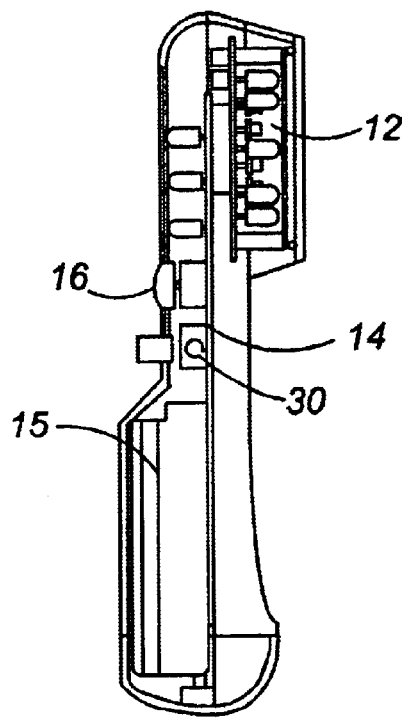
FIG. 3 is a sectional view taken along line 3—3 of FIG. 1.

Referring now to FIGS. 1 to 3, therapeutic low level laser apparatus embodying features of the present invention includes a housing 11, a diode array 12, control electronics 14, an electric power source 15, a means for operator input 16 and a means for operator output 17. Housing 11 is generally elongated, has a front 20 and a back 21, and is preferably sized and shaped to be comfortably held in the hand of an operator. Other sizes and shapes are suitable for housing 11.

Figure 4:
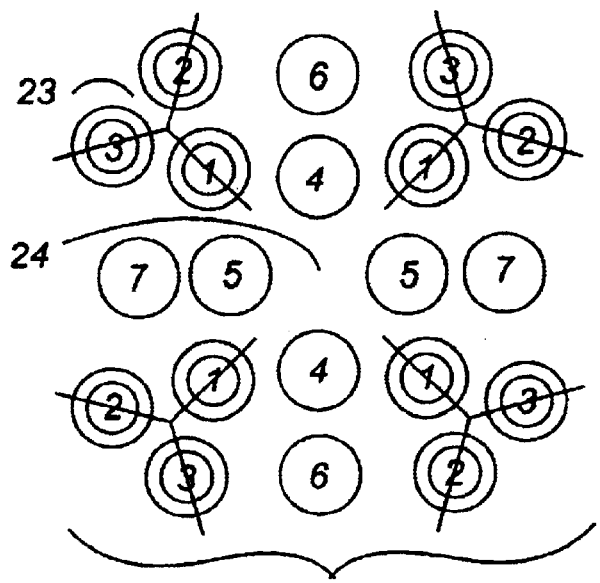
FIG. 4 is a diagrammatic view of the diode array of the apparatus of FIG. 1.

The diode array 12 is substantially planar and is mounted in a recessed manner in the back 21 of the housing 11. The diode array includes four each first, second and third laser diodes 1, 2 and 3, and two each first, second, third and fourth light emitting diodes 4, 5, 6 and 7 that, in the illustrated embodiment, emit the following wavelengths:

1=650 nm laser diode
2=780 nm laser diode
3=808 nm laser diode
4=660 nm light emitting diode
5=880 nm light emitting diode
6=470 nm light emitting diode
7=940 nm light emitting diode As shown in FIG. 4, the first, second and third laser diodes 1, 2 and 3 are arranged in four sets 23, with one set 23 at each of 45, 135, 225, and 315 degrees about the center 24 of the diode array 12. Each set 23 is arranged as an equilateral triangle with the first laser diodes 1 each an equal first distance from center 24 and the second and third laser diodes 2 and 3 an equal greater second distance from center 24. The first, second and third laser diodes 1, 2 and 3 of each set 23 are oriented at 120 degrees to each other, as indicated by the lines through the first, second and third laser diodes 1, 2 and 3 in FIG. 4, with the first laser diodes 1 being oriented along lines through center 24. The first, second, third and fourth light emitting diodes 4, 5, 6 and 7 are arranged in a cross formation between the sets 23 with equal wavelengths being mirrored or opposed across center 24.

Referring again to FIGS. 1 to 3, the control electronics 14 and power source 15 mount in the housing 11 with the power source 15 connecting to and powering the control electronics 14. The power source 15 is preferably a rechargeable storage battery and is preferably rechargeable without removal from the housing 11. The control electronics 14 connect to and provide electric power to diode array 12 to individually activate and control the intensity of each of the first, second and third laser diodes 1, 2 and 3, and each of the first, second, third and fourth light emitting diodes 4, 5, 6 and 7. The control electronics 14 include current monitoring to assure precise intensity control. The control electronics 14 can pulse each of the first, second and third laser diodes 1, 2 and 3, and each of the first, second, third and fourth light emitting diodes 4, 5, 6 and 7 at a frequency of from about 0.1 Hz to 300 kHz in 0.01 Hz increments.

The control electronics 14 is programmable and, in the illustrated embodiment, includes three preprogrammed modes:

Mode 1: Frequency=50 Hz, duration=3 minutes, power=all lasers set at 1 to 4 mW.

Mode 2: Frequency=7.83 Hz, duration=3 minutes, power=all lasers set at 1 to 4 mW.

Mode 3: Frequency=see below, total duration=3 minutes, power=all lasers set at 1 to 4 mW.

1. 17.16 sec—4.3 Hz
2. 5.72 sec each for 28 increments that increase from 4.7 Hz to 130.2 Hz.

The means for operator input 16 is connected to the control electronics 14 and in the illustrated embodiment includes an on/off button 27, a function button 28 and a mode button 29. Other means for operator input 16 are suitable, such as additional buttons, a keypad, or a jack for connection to a keyboard or a personal computer.

The means for operator input 16 also includes a jack 30 for connection of a calibration device that allows the manufacturer to calibrate the diode array 12 and to download operation modes such as listed above. The jack 30 may also be used by an operator to download new modes. By way of example, and not as a limitation, the calibration device may be a personal computer. The means for operator output 17 is mounted on the front 20 of housing 11, connected to the control electronics 14 and, in the illustrated embodiment, includes a mode indicator 32, a battery indicator 33 and a time remaining indicator 34.

The first, second and third laser diodes 1, 2 and 3, and the first, second, third and fourth light emitting diodes 4, 5, 6 and 7 emit beams normal to the plane of the diode array 12. The configuration of the diode array 12 provides four "hot spots" where the beams of the first, second and third laser diodes 1, 2 and 3 overlap. Due to the "Soliton Phenomenon", where multiple overlapping waveforms create unique wave structures capable of imparting effects unattainable with individual waveforms, improved penetration into tissue is provided.

The method of the present invention includes the steps of: providing a diode array with sets of first, second and third laser diodes that emit at wavelengths of about 650 nm, 780 nm and 808 nm, respectively, with the beams of the first, second and third laser diodes oriented at about 120 degrees relative to each other and overlapping, pulsing the first, second and third laser diodes at a selected frequency sequence and projecting the resultant beam on the tissue. The first, second and third laser diodes may be pulsed according to the above described modes as well other modes.

Although the present invention has been described with a certain degree of particularity, it is understood that the present disclosure has been made by way of example and that changes in details of structure may be made without departing from the spirit thereof.

I claim:

1. A therapeutic laser system, comprising:
   a housing sized and shaped to be comfortably held in the hand of an operator, and having a front and a back, and
   a substantially planar diode array mounted in a recessed manner on said back of said housing, and having a center and four sets of laser diodes each having a first, second and third laser diode, each said set being arranged in an equilateral triangle, said sets being equally spaced about said center with said first laser diodes of each said set being spaced a first distance from said center of said diode array, and said second and third laser diodes being spaced a greater second distance from said center of said diode array, and each of said first, second and third laser diodes having a beam, said beams overlapping,
   whereby said diode array projects a resultants composite beam that is directed at selected tissue to impart energy into said tissue.

2. The laser system as set forth in claim 1 wherein said first, second and third laser diodes of each said set each have a different wavelength.

3. The laser system as set forth in claim 2 wherein each said first laser diode has a wavelength of 650 nm, each said second laser diode has a wavelength of 780 nm, and each said third laser diode has a wavelength of 808 nm.

4. The laser system as set forth in claim 1 wherein said diode array includes two each first, second, third and fourth light emitting diodes arranged in a cross formation between said sets of laser diodes and mirrored across said center.

5. The laser system as set forth in claim 4 wherein said first light emitting diodes have a wavelength of 660 nm, said second light emitting diodes have a wavelength of 880 nm, said third light emitting diodes have a wavelength of 470 nm, and said fourth light emitting diodes have a wavelength of 940 nm.

6. The laser system as set forth in claim 1 including an electric power source mounted in said housing, and
   programmable control electronics mounted in said housing, connected to and powered by said power source, and connected to and providing electric power to each of said first, second and third laser diodes to individually activate and control the intensity of each of said first, second and third laser diodes.

7. The laser system as set forth in claim 6 wherein said control electronics includes a plurality of preprogrammed modes for activating said first, second and third laser diodes.

8. The laser system as set forth in claim 7 including means for operator input connected to said control electronics, for operator control of said control electronics.

9. The laser system as set forth in claim 8 wherein said means for operator input has an on/off button mounted on said front of said housing for turning said control electronics on and off, and a mode button mounted on said front of said housing for selecting one of said modes.

10. The laser system as set forth in claim 9 wherein said means for operator input includes a jack mounted on said housing for connection to a calibration device for calibrating said diode array through said control electronics and downloading additional said modes to said control electronics.

11. The laser system as set forth in claim 7 including means for operator output mounted on said front of said housing and connected to said control electronics, for advising an operator of the status of said control electronics and said diode array.

12. The laser system as set forth in claim 11 wherein said means for operator output includes a mode indicator, a battery indicator and a time remaining indicator.

13. A therapeutic laser system, comprising:
   a housing sized and shaped to be comfortably held in the hand of an operator, and having a front and a back,
   a substantially planar diode array mounted in a recessed manner on said back of said housing, and having a center, four sets of laser diodes each having a first, second and third laser diode, the beams of said laser diodes overlaping within each set, and two each first, second, third and fourth light emitting diodes, each said set being arranged in an equilateral triangle, said sets being equally spaced about said center with said first laser diodes of each said set being spaced a first distance from said center of said diode array, and said second and third laser diodes being spaced a greater second distance from said center of said diode array, each said set having a center with said first, second and third laser diodes of each set being oriented at 120 degrees to each other along lines through said center of said set, said first, second, third and fourth light emitting diodes being arranged in a cross formation between said sets of laser diodes and mirrored across said center, each said first laser diode having a wavelength of 650 nm, each said second laser diode having a wavelength of 780 nm, and each said third laser diode having a wavelength of 808 nm, said first light emitting diodes having a wavelength of 660 nm, said second light emitting diodes having a wavelength of 880 nm, said third light emitting diodes having a wavelength of 470 nm, said fourth light emitting diodes having a wavelength of 940 nm, an electric power source mounted in said housing, programmable control electronics mounted in said housing, connected to and powered by said power source, and connected to and providing electric power to each of said first, second and third laser diodes and said first, second, third and fourth light emitting diodes to individually activate and control the intensity of each of said first, second and third laser diodes and said first, second, third and fourth light emitting diodes, said control electronics including a plurality of preprogrammed modes for activating said first, second and third laser diodes and said first, second, third and fourth light emitting diodes, means for operator input connected to said control electronics, for operator control of said control electronics, said means for operator input having an on/off button mounted on said front of said housing for turning said control electronics on and off, a mode button mounted on said front of said housing for selecting one of said modes, and a jack mounted on said housing for connection to a calibration device for calibrating said diode array through said control electronics and downloading additional said modes to said control electronics, and means for operator output mounted on said front of said housing and connected to said control electronics, for advising an operator of the status of said control electronics and said diode array, said means for operator output including a mode indicator, a battery indicator and a time remaining indicator, whereby said diode array projects a resultant composite beam that is directed at selected tissue to impart energy into said tissue.

14. A method of laser therapy comprising the steps of:

providing a diode array having a center and four sets of laser diodes each having a first, second and third laser diode, each said set being arranged in an equilateral triangle, said sets being equally spaced about said center with said first laser diodes of each said set being spaced a first distance from said center of said diode array, and said second and third laser diodes being spaced a greater second distance from said center of said diode array, said first, second and third laser diodes of each set each having laser beams and being oriented such that in each said set said laser beams are oriented at about 120 degrees relative to each other and overlapping, pulsing said first, second and third laser diodes according to a selected frequency sequence, and projecting the resultant beam on selected tissue to impart energy into said tissue.

15. The method of laser therapy as set forth in claim 14 wherein each said first laser diode has a wavelength of 650 nm, each said second laser diode has a wavelength of 780 nm, and each said third laser diode has a wavelength of 808 nm.

16. The method of laser therapy as set forth in claim 14 wherein said frequency sequence includes pulsing said first, second and third laser diodes at 4.3 Hz for 17.16 sec then pulsing for 5.72 sec each for 28 increments from 4.7 Hz to 130.2 Hz.

17. A method of laser therapy comprising the steps of:

providing a diode array having a center and four sets of laser diodes each having a first, second and third laser diode, each said set being arranged in an equilateral triangle, said sets being equally spaced about said center with said first laser diodes of each said set being spaced a first distance from said center of said diode array, and said second and third laser diodes being spaced a greater second distance from said center of said diode array, said first, second and third laser diodes of each set each having laser beams and being oriented such that in each said set said laser beams are oriented at about 120 degrees relative to each other and overlapping, each said first laser diode having a wavelength of 650 nm, each said second laser diode having a wavelength of 780 nm, and each said third laser diode having a wavelength of 808 nm pulsing said first, second and third laser diodes at 4.3 Hz for 17.16 sec then pulsing for 5.72 sec each for 28 increments from 4.7 Hz to 130.2 Hz, and projecting the resultant beam on selected tissue to impart energy into said tissue.

* * * * *